United States Patent [19]
Monnier

[11] 4,454,874
[45] Jun. 19, 1984

[54] PLASTER SPLINT OR CAST FOR MEDICAL PURPOSES

[76] Inventor: Peter L. Monnier, 81 Pocahontas Rd., Redding, Conn. 06896

[21] Appl. No.: 443,296

[22] Filed: Nov. 22, 1982

[51] Int. Cl.³ .............................................. A61F 5/04
[52] U.S. Cl. .................................................. 128/91 R
[58] Field of Search .................. 128/91 R, 156, 87 R, 128/89 R, 90, 155

[56] References Cited

U.S. PATENT DOCUMENTS 3,923,049 12/1975 Lauber et al. ..................... 128/91 R
4,126,130 11/1978 Cowden et al. ................... 128/91 R
4,235,228 11/1980 Gaylord, Jr. et al. ............. 128/91 R

FOREIGN PATENT DOCUMENTS 1098164 1/1961 Fed. Rep. of Germany .... 128/91 R

*Primary Examiner*—John D. Yasko

[57] ABSTRACT

A blank from which a plaster splint or cast is formed on an injured member consists of a strip, or stack of strips, of fabric impregnated with dry powdered plaster of paris enclosed between two sheets of non-water-absorptive material. The sheets are joined at their side edges to retain the fabric strip between them. The sheet which will be at the outward side of the completed splint or cast is perforated to enable water to be applied through it to wet the plaster powder.

The other sheet, which will be at the inward side of the completed splint or cast adjacent to the member on which the splint or cast is applied, has discrete cushion elements spaced apart over it. These cushion elements provide padding between the splint or cast and the member and also permit air circulation in the interface between the splint or cast and the member. A heat barrier is provided between the plaster and the member on which the splint or cast is formed for shielding the member from the heat that is generated by the setting and hardening of the plaster.

In use the plaster in the blank is wetted to become paste. The blank is then laid on the member that is to have the splint or cast applied to it and is shaped to conform to the member while the plaster is still soft. The plaster sets and hardens with the splint or cast in place on the member.

10 Claims, 4 Drawing Figures

PLASTER SPLINT OR CAST FOR MEDICAL PURPOSES

BRIEF SUMMARY OF THE INVENTION

This invention relates to plaster splints or casts of the type used in medical practice for immobilizing and supporting an injured member, such as a person's arm or leg. In particular the invention is a blank that is ready to be formed into a splint or cast by wetting and shaping onto the member to which the splint or cast is to be applied.

This invention may be adapted for forming either splints or casts of plaster for medical or other purposes. For convenience the invention will hereinafter be described primarily with reference to splints, but it is to be appreciated that the term splint as used hereinafter is intended also to imply the term cast.

In medical practice splints or casts for an injured member are conventionally constructed by laying a piece of soft fabric, such as flannel, on the injured member and then laying on successive layers of gauze impregnated with wet plaster until enough layers are built up to provide the desired strength and stiffness for the finished splint when the plaster sets and hardens. The plaster is allowed to harden with the splint in place on the member.

Efforts to simplify the foregoing procedure have been made by providing splint blanks consisting of stacks of strips of gauze impregnated with powdered plaster of paris enclosed in sleeves of water absorbent material. To use these blanks they are soaked in water to wet the plaster; when the plaster is thoroughly wetted the excess water is squeezed out and the blank is laid on shaped to conform to the member that is to be splinted. The plaster is allowed to set and harden with the splint in place on the member. Blanks of this type for casts or splints are disclosed in U.S. Pat. Nos. 3,900,024 and 3,923,049.

Splints formed by the previously used techniques, including use of blanks of the type just described, have a number disadvantages. In particular in these previously used types of splints the inside surface of the splint which is against the surface (i.e. skin) of the member being splinted is wet when the splint is first applied and must dry while in contact with that member surface. The combination of this wetness and the heat generated by the setting and hardening of the plaster creates the type of warm, moist enclosed environment at the interface between the splint and the splinted member which is ideally suited for, and which stimulates the growth of, mold or bacteria that may cause serious infection, or at least cause itching or other discomfort. Also the considerable amount of heat generated by the setting plaster may itself cause discomfort.

The foregoing and other disadvantages inherent is the previously used types of splints just described are avoided with the splint blank of the present invention which consists essentially of a strip, or stack of strips, of fabric impregnated with dry powdered plaster enclosed between two sheets of flexible, non-water-absorptive material. The side edges, and preferably also the end edges, of the sheets are joined together to retain the plaster impregnated fabric between them.

The sheet which will be at the outward side of the splint that is to be formed on a member is perforated for water to be applied through the perforations to wet the powdered plaster and thus prepare the blank to be formed into a splint on the member to be splinted. The other sheet, which will be the inward surface of the finished splint facing and adjacent to the surface of the splinted member, has discrete cushion elements spaced over its surface to provide padding between the splint and the member and also to permit air to circulate between the cushion elements at the interface between the splint and the member.

In the preferred form of the invention a heat barrier is provided between the plaster impregnated fabric strip and the side of the splint blank which will be facing and adjacent to the spinted member. This heat barrier thus shields the member from the heat that is generated by the setting of the plaster. The heat barrier may be provided by a separate sheet of heat reflective material (e.g. a plastic sheet with a reflective coating thereon) or by providing the inner surface of the sheet which will be adjacent to the splinted member with a heat reflective coating, as by 'silvering' the latter surface by vapor deposition of aluminum thereon, for example.

Shielding the member from heat generated by the setting plaster eliminates discomfort that might be caused by that heat; in addition, and in combination with the air circulation provided for at the interface between the splint and the splinted member by the cushion elements, prevents or inhibits the creation of a stagnant, warm moist environment at that interface and thereby prevents or inhibits the growth of mold there which could cause serious infection or at least itching and discomfort.

BRIEF DESCRIPTION OF THE VIEWS OF THE DRAWINGS

The invention is described below in more detail with reference to a preferred embodiment of the invention illustrated by the accompanying drawings in which.

DETAILED DESCRIPTION

Figure 1:
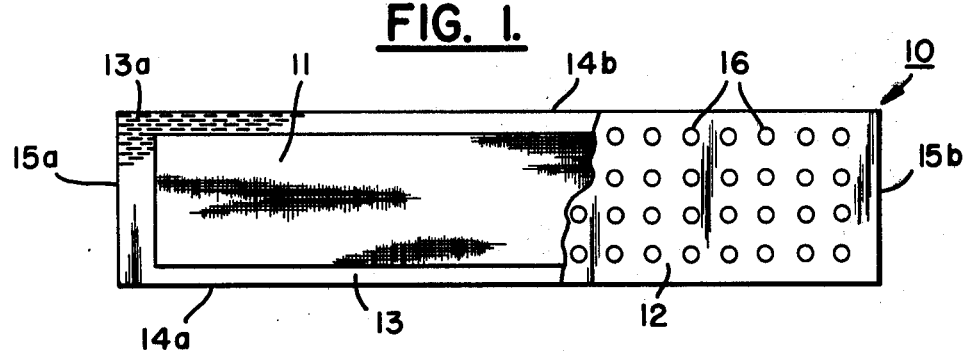
FIG. 1 is a top plan view, partly broken away, of a splint blank in accordance with this invention.
Figure 2:
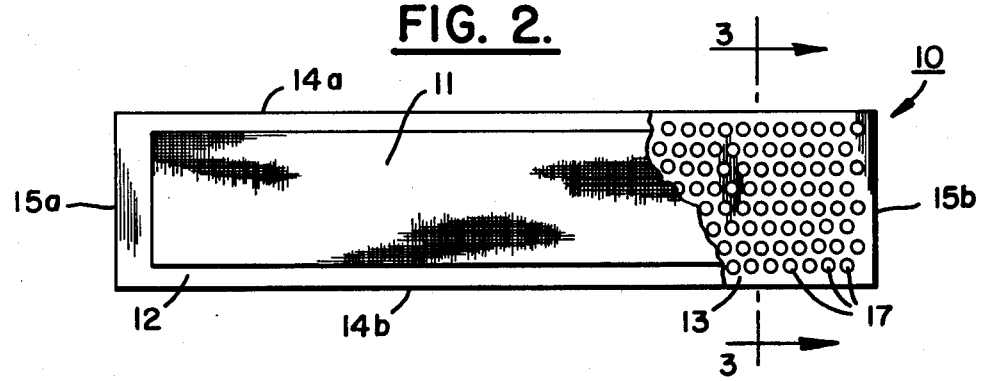
FIG. 2 is a plan view, partly broken away, of the bottom of the splint blank shown in FIG. 1.
Figure 3:
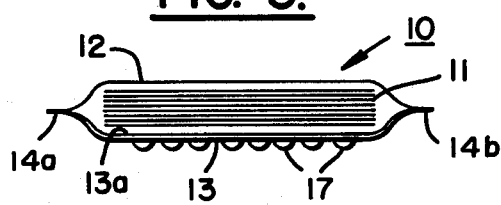
FIG. 3 is a sectional view along the line 3—3 of FIG. 2.

Referring now to FIGS. 1 and 3 of the drawings a splint blank 10 of this invention is made up of a strip 11 of fabric 11 impregnated with powdered plaster and enclosed between two sheets, 12 and 13, of flexible, non-water-absorptive material, such as polyethylene or other plastic.

The strip 11 of fabric is suitably provided by a number of layers of gauze, each impregnated with plaster, in a stack. The plaster is normally dry powdered plaster of paris (calcined gypsum) or the like which when wetted with water forms a paste which may be shaped and which then sets and hardens into a cohesive, hard mass.

The number of layers of gauze strips in the strip of fabric 11, as well as the length and width of the strip 11, is determined by the type of member on which the splint is to be formed and the weight and abuse the splint will have to bear. For example, a splint blank 10 for an average adult's arm might suitably be formed by a stack of ten strips of plaster impregnated gauze four inches wide and eighteen inches long forming the strip 11 of fabric. For a leg splint the strip 11 might be made up of a stack of fifteen layers of plaster impregnated gauze six to eight inches wide and perhaps thirty inches long.

The sheets 12 and 13 which enclose the plaster impregnated strip 11 of fabric are wider, and preferably longer, than the strip 11 and are joined together at at least their opposite side edges as indicated at 14a and 14b. These edges may be joined by heat sealing, in the case of plastic sheets 12 and 13, or by stitching, gluing or other effective joining means.

It is preferred to have the sheets 12 and 13 longer than the fabric strip 11 and to have the ends of the sheets 12 and 13 also joined together, as indicated at 15a and 15b, so that the fabric strip 11 is completely retained between the sheets 12 and 13. In this case each splint blank 10 would be performed a selected length, width and number of gauze strips in the strip 11 to adapt it for use for splinting a particular type of member, such as an adult arm. As an alternative the blank 10 could be made a selected width and thickness but of an indefinite length rolled up in a roll. For use a section of the blank would be unrolled and cut the desired length. In this instance it would still be desirable, though not absolutely necessary, to join the cut ends of the sheets 12 and 13 to enclose the cut ends of the fabric strip 11. For this purpose the cut ends of the fabric strip 11 could be pushed inward to enable the cut ends of the sheets 12 and 13 to be more easily brought together and joined, as by heat sealing, for example.

Figure 4:
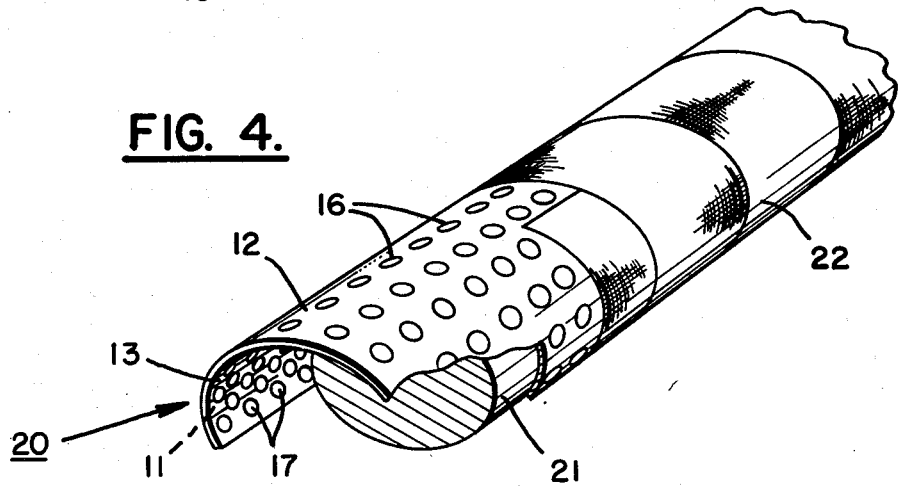
FIG. 4 is a perspective view, partly broken away and partly in section, showing a completed splint formed with a blank of this invention, showing it as applied on a member, such as a person's arm, to immobilize and support the member.

As shown in FIG. 1 and 4 the flexible, non-water-absorptive sheet 12 which will be facing outward at the outside of a splint formed on a member (splint 20 on member 21 in FIG. 4) is perforated as indicated by perforations 16 for the purpose of applying water through the perforations to wet the plaster in strip 11 when the splint is to formed.

The other sheet, sheet 13, which will be at the inner surface of the completed splint, against the surface (i.e. skin) of the member 21, has a plurality of discrete cushion elements 17 spaced apart over its surface. These cushion elements 17 may be formed by discrete bubbles of air trapped between two sheets of plastic that are laminated to form the sheet 13.

Referring to FIG. 4 a splint 20 is formed from a blank 10 of this invention by applying water through the perforations 16 in sheet 12 to wet the plaster powder in the fabric strip 11. This may be done by dipping the blank 10 in a pan of water or by squeezing a wet sponge against the sheet 12 so that water presses through the perforations 16 to wet the plaster and turn it into a paste. The blank may be kneaded to thoroughly wet all the plaster. Excess water is then squeezed or blotted out. While the plaster is soft and workable the blank 10 is laid on the member to be splinted and shaped to conform to the member which has previously been placed in the position in which it is to be immobilized by the splint. The plaster sets and hardens with the splint 20 in place; the splint 20 may be held in place on the member 21 by wrapping with bandage 22 as indicated in FIG. 4.

As the plaster sets and hardens it generates considerable heat which could cause discomfort to the member. Therefore in a preferred form of the the splint blank 10 of this invention a heat barrier is provided to be between the plaster impregnated strip 11 and the member 21 on which the splint 20 is placed. The heat barrier may be a separate sheet (not shown) of a heat reflective material, such as a sheet of plastic with a coating of a heat reflective material such as aluminum, between the plaster impregnated fabric strip 11 and the sheet 13 which will be at the inner side of the completed splint 20. Alternatively, and as indicated in the drawings, the heat barrier may be provided by 'silvering' the surface 13a (FIGS. 1 and 3) of sheet 13 which is adjacent to the plaster impregnated fabric strip 11. This 'silvering' may be done by vapor deposition of aluminum on the surface 13a.

As indicated in FIG. 4 the cushion elements 17 on sheet 13 form padding between the splint 20 and the member 21. Moreover, since the cushion elements are discrete and spaced apart they provide passages for air to circulate through the interface between the splint 20 and the skin surface of member 21. This air circulation along with the blocking of heat from this interface by the action of the heat barrier surface 13a prevents the collection of heat and moisture at this interface and thus prevents or inhibits the growth of mold or bacteria which could cause severe infection, or at least cause itching and discomfort.

What is claimed is:

1. A blank adapted to be formed into a plaster splint to be placed on a member, such as a person's arm or leg, comprising in combination:
    a strip of fabric impregnated with powdered plaster that will absorb and react with water to set into a cohesive, substantially rigid mass,
    a first sheet and a second sheet of flexible, non-water-absorptive material enclosing said strip between them with said sheets being joined together along at least their side edges at opposite side edges of said fabric strip,
    said first sheet, which forms the outside of a completed splint facing outward of the member on which said splint is placed, being perforated to enable water to be applied through said perforations to set said plaster, and
    said second sheet, which forms the inward side of a completed splint facing inward toward said member on which said splint is placed, having a plurality of cushion elements thereon.

2. The blank of claim 1 in which said cushion elements are discrete and spaced apart on said second sheet to provide passages between them.

3. The blank of claim 1 in which said cushion elements are discrete air-filled chambers.

4. The blank of claim 1 which includes a heat barrier between said second sheet and said plaster impregnated fabric strip for shielding a member on which said splint is placed from heat generated by the setting and hardening of said plaster.

5. The blank of claim 4 in which said heat barrier is provided by heat reflective material on a surface of said second sheet that faces said plaster impregnated fabric strip.

6. The blank of claim 4 in which said heat barrier is a coating of heat reflective material on the surface of said second sheet that faces said plaster impregnated fabric strip.

7. A blank adapted to be formed into a plaster splint to be placed on a member, such as a person's arm or leg, comprising in combination:
    a strip of fabric impregnated with powdered plaster that when wetted with water sets into a cohesive rigid mass, a first sheet and a second sheet of flexible, non-water-absorptive material enclosing said strip of fabric between them with said sheets being joined together at their side edges to retain said strip between them, said first sheet, which will form the outside of a completed splint facing outward of the member on which said splint is placed, being perforated to enable water to be applied through said perforations to wet said plaster, and a heat barrier between said second sheet and said strip of plaster impregnated fabric for shielding a member on which said splint is placed from heat generated by the setting and hardening of said plaster.

8. The blank of claim 7 in which said second sheet, which forms the inside of a completed splint facing inward toward said member on which said splint is placed, is padded.

9. The blank of claim 8 in which said second sheet is padded by having discrete cushion elements spaced apart on it.

10. The blank of claim 9 in which said cushion elements are air-filled chambers.